(12) United States Patent
Smith (10) Patent No.: US 8,097,146 B2
(45) Date of Patent: Jan. 17, 2012

(54) DEVICE AND METHOD FOR MONITORING AN ELECTROCHEMICAL GAS SENSOR

(75) Inventor: Patrick G. Smith, Shakopee, MN (US)

(73) Assignee: Sensor Electronics Corporation, Minneapolis, MN (US)

( * ) Notice: Subject to any disclaimer, the term of this patent is extended or adjusted under 35 U.S.C. 154(b) by 941 days.

(21) Appl. No.: 12/056,876

(22) Filed: Mar. 27, 2008

(65) Prior Publication Data

US 2009/0242398 A1  Oct. 1, 2009

(51) Int. Cl.
G01N 27/404 (2006.01)

(52) U.S. Cl. .................. 205/775; 204/401

(58) Field of Classification Search .......... 204/421–429, 204/401, 431, 432; 205/781, 783.5, 784.5, 205/775
See application file for complete search history.

(56) References Cited

U.S. PATENT DOCUMENTS

| | | | |
|---|---|---|---|
| 3,661,748 A * | 5/1972 | Blackmer | 204/401 |
| 5,202,637 A | 4/1993 | Jones | |
| 5,403,452 A * | 4/1995 | Hielscher et al. | 205/781 |
| 5,466,356 A | 11/1995 | Schneider et al. | |
| 5,558,752 A * | 9/1996 | Wang et al. | 204/401 |
| 5,611,909 A | 3/1997 | Studer | |
| 5,753,101 A * | 5/1998 | Ludwig | 205/781 |
| 6,123,818 A | 9/2000 | Lindsay | |
| 6,200,443 B1 | 3/2001 | Shen et al. | |
| 6,251,243 B1 | 6/2001 | Lindsay | |
| 6,428,684 B1 | 8/2002 | Warburton | |
| 7,033,482 B2 | 4/2006 | Inoue | |
| 7,090,755 B2 | 8/2006 | Inoue et al. | |
| 7,185,533 B2 | 3/2007 | Lee et al. | |
| 7,190,988 B2 | 3/2007 | Say et al. | |
| 7,195,704 B2 | 3/2007 | Kermani et al. | |
| 7,199,594 B2 | 4/2007 | Kermani | |
| 7,209,850 B2 | 4/2007 | Brott et al. | |
| 7,211,987 B2 | 5/2007 | Aoki et al | |
| 7,217,354 B2 | 5/2007 | Mahurin et al. | |
| 7,297,240 B2 | 11/2007 | Hattori | |
| 7,297,242 B2 | 11/2007 | Tice | |
| 2006/0091007 A1 | 5/2006 | Inoue et al. | |
| 2007/0102292 A1 | 5/2007 | Dreibholz et al. | |
| 2007/0125665 A1 | 6/2007 | Kubinski et al. | |
| 2007/0236224 A1 | 10/2007 | Augustyniak et al. | |
| 2007/0261475 A1 | 11/2007 | Allmendinger | |
| 2008/0000779 A1 | 1/2008 | Wang et al. | |

* cited by examiner

*Primary Examiner* — Kaj K Olsen
*Assistant Examiner* — Kourtney R Salzman
(74) *Attorney, Agent, or Firm* — Allison Johnson, P.A.

(57) ABSTRACT

An electrochemical gas sensor testing device that includes a test signal generator that generates a multiplexed signal that includes a first test signal that includes alternating current (AC) and is free from a direct current (DC) component and a second signal that includes a DC bias voltage, an electrochemical cell that includes a counter electrode, a sensing electrode, and an electrolyte, the counter electrode and the sensing electrode being in electrical communication with the electrolyte and each other, the counter electrode being in electrical communication with the signal generator to receive the multiplexed signal generated by the signal generator, and a processor that receives an AC signal from the sensing electrode and that analyzes the AC signal.

14 Claims, 7 Drawing Sheets

$V_{Test}$ $V_0$ Good $V_0$ Fail

DEVICE AND METHOD FOR MONITORING AN ELECTROCHEMICAL GAS SENSOR

BACKGROUND

The invention relates to monitoring the function of an electrochemical gas sensor.

Many work place and production environments are monitored for the presence of potentially dangerous gas mixtures. Electrochemical gas sensors are often used to detect the presence of one or more gases in an environment. Electrochemical gas sensors usually give an electrical response that is proportional upon the concentration of the gas being detected. Electrochemical gas sensors include an electrochemical cell that includes a sensing electrode (which is also referred to as the working electrode), a counter electrode and an electrolyte. Some electrochemical cells also include a third electrode that is referred to as the reference electrode. An external voltage is applied to the reference electrode to bias the redox reaction. During cell operation, when a gas dissolves into the electrolyte, an oxidation reaction occurs at one electrode and a reduction reaction occurs at the other electrode. This is referred to as the "redox" reaction. Electrons flow from the oxidizing electrode to the reducing electrode. This electron flow (i.e., electrical current) is then measured, which measurement is then translated into the concentration of gas detected.

Electrochemical cells eventually fail due to a variety of causes including, e.g., the electrolyte drying up, the electrolyte becoming contaminated, and the electrodes becoming physically disconnected. In many cases, the failure goes unnoticed. Unfortunately, in many cases when failure occurs no current flows, which is the same thing that occurs when no gas is present in the system. In addition, in many failure situations, the cell becomes unresponsive to the target gas, i.e., the gas that the cell was designed to detect. As a result, the signal produced as a result of a failure is the same signal that is produced when gas is being detected (i.e., no current flow), and for this reason the failure may go undetected.

Various mechanisms are used to address the fact that electrochemical cells fail. In some cases, the cell has a fixed service life or a limited lifetime and the user simply disposes of the cell after a predetermined period of time and replaces it with a new one, regardless of whether or not the cell is still functioning. Some electrochemical cells are equipped with a gas generating cell that operates in reverse of the electrochemical cell. Rather than generating a redox current when gas is applied, it generates gas when current is applied. The gas generating cell is actuated periodically to determine the viability of the sensing cell. Other techniques rely on a calibration of the cell at fixed time intervals or a "bump" test. A bump test typically involves exposing the electrochemical cell to a test gas mixture for a period of time sufficient to activate the warning alarms and/or other modes of display that indicate that the instrument is responding correctly to the gas. The bump test is usually quicker than a calibration, but it still involves the expense of both time and test gas mixtures.

Many methods for testing electrochemical cells involve applying a DC test signal using a dedicated circuit, i.e., a circuit whose sole function is to generate and send the test signal. The dedicated test circuit is separate from the circuit that biases the electrochemical cell. Examples of such test circuits are described in U.S. Pat. No. 6,428,684 (Warburton).

It would be desirable to have a simple test that can be performed automatically without human intervention for determining whether or not an electrochemical cell is functioning properly. It would also be desirable if such a test could be performed without interrupting the gas detection function of the sensor and by the existing circuitry of the electrochemical gas sensor.

SUMMARY

In a first aspect, the invention features an electrochemical gas sensor testing device that includes a signal generator that generates a multiplexed signal that includes a first test signal that includes alternating current (AC) and is free of a direct current (DC) component, and a second signal that includes a DC bias voltage, an electrochemical cell that includes a counter electrode, a sensing electrode, and an electrolyte, the counter electrode and the sensing electrode being in communication (e.g., electrical) with the electrolyte and each other, the counter electrode being in communication (e.g., electrical) with the signal generator to receive the multiplexed signal generated by the signal generator, and a processor that receives an AC signal from the sensing electrode and that analyzes the AC signal. In one embodiment, the device further includes a filter that transmits alternating current and blocks direct current. In another embodiment, the device further includes a filter that blocks alternating current and transmits direct current. In some embodiments, the device further includes a filter that blocks alternating current and transmits direct current and a filter that blocks direct current and transmits alternating current. In other embodiments, the processor instructs the signal generator to generate the test signal.

In one embodiment, the processor simultaneously analyzes a DC signal corresponding to the concentration of gas present in the electrochemical cell and the AC signal. In another embodiment, the processor compares a first AC signal that corresponds to the AC test signal to a second AC signal that corresponds to the AC test signal (e.g., a stored test signal corresponding to a test signal received at a point earlier in time that the second AC signal).

In some embodiments, a single signal generator generates both the AC test signal and the DC bias voltage. In one embodiment, the single signal generator is a potentiometer. In other embodiments, the single signal generator is a variable gain amplifier.

In another aspect, the invention features a method of testing an electrochemical gas sensor, the method including simultaneously applying an alternating current test signal and a direct current bias voltage to a counter electrode of an electrochemical gas sensor, the electrochemical gas sensor including a sensing electrode, an electrolyte, and the counter electrode, transmitting the AC test signal from the sensing electrode to a processor, analyzing the AC signal received by the processor, and determining whether or not the electrochemical cell is functioning. In one embodiment, the method further includes comparing at least one frequency of an AC test signal transmitted to the processor at a first time to the same at least one frequency of an AC signal transmitted to the processor at a second time later than the first time. In another embodiment, the method further includes simultaneously analyzing a DC signal corresponding to the concentration of a gas present in the electrochemical cell and the AC signal corresponding to the AC test signal.

In one embodiment, the processor simultaneously receives a DC signal corresponding to the concentration of a gas present in the electrochemical cell and an AC signal corresponding to the AC test signal.

In other embodiments, the method further includes storing a signal corresponding to the AC test signal. In another embodiment, the method further includes comparing a received AC signal corresponding to the AC test signal to the stored AC test signal. In one embodiment, the method further includes comparing a frequency of a received AC signal corresponding to the AC test signal to the stored signal (e.g., same frequency of the stored signal).

In some embodiments, when no AC signal is received by the processor, a signal is generated indicating that the cell is not functioning properly. In other embodiments, the AC test signal includes multiple frequencies. In one embodiment, the AC test signal includes constant frequency and amplitude.

In other embodiments, the method further includes applying the AC test signal continuously to the electrochemical cell.

In other aspects, the invention features an electronic circuit that includes an electrochemical cell, and a single signal generator that applies an AC test signal and a DC bias voltage to the electrochemical cell. In one embodiment, the signal generator applies the AC test signal and the DC bias voltage simultaneously to the electrochemical cell.

In another embodiment, the signal generator is a variable gain amplifier. In other embodiments, the signal generator is a potentiometer. In another embodiment, the circuit further includes a processor that instructs the signal generator to generate the test signal.

The invention features the application of an AC test signal to an electrochemical cell of a gas sensor that does not interfere with the gas detection function of the sensor and that indicates whether or not a cell is working, failing or has failed. The invention also features a method of testing an electrochemical cell of a gas sensor where the method can be conducted at the same time the cell is detecting a gas of interest.

The invention also features the application of a multiplexed signal to an electrochemical cell of a gas sensor where the multiplexed signal includes both an AC test signal that is free of a DC component, and a DC bias voltage.

The invention features the ability to utilize the existing bias voltage circuit of an electrochemical cell of a gas sensor to apply a multiplexed signal that includes the AC test signal. Therefore the test method can be conducted without adding a separate test circuit. The invention also features a test signal that can be tailored to a particular cell's parameters.

Other features and advantages will be apparent from the following description of the drawings, the preferred embodiments, and from the claims. In the figures, like numbers are used to represent like elements.

DETAILED DESCRIPTION

The electrochemical gas sensor testing device tests the electrochemical cell of a gas sensor to determine whether or not the cell is functioning properly, i.e., able to detect a gas of interest in the environment to which it is exposed. The device can be configured to test the electrochemical cell while the electrochemical cell is detecting the presence of a gas of interest. In other words, the test of the electrochemical cell function can occur without interfering with the gas sensing function of the cell.

Figure 1:
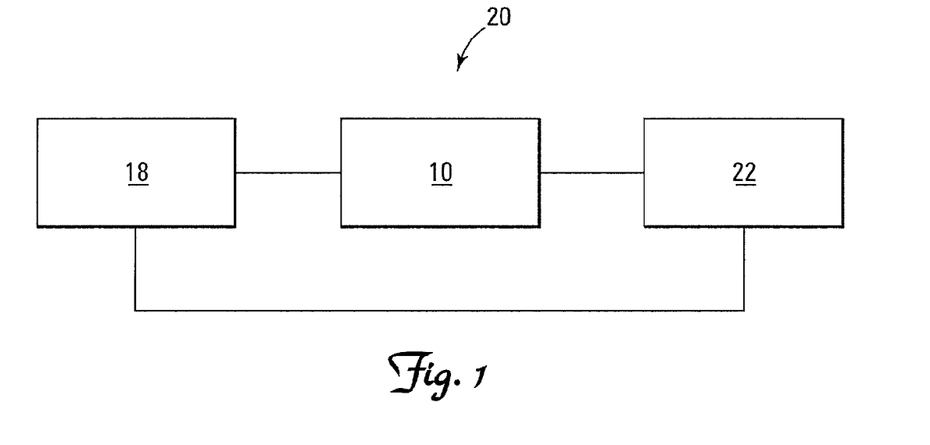
FIG. 1 is a block diagram of an electrochemical gas sensor test device.
Figure 2:
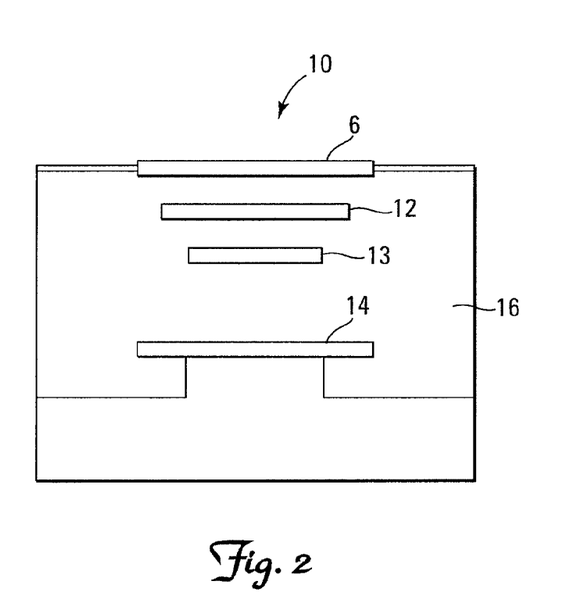
FIG. 2 is a schematic diagram of the electrochemical cell of the device of FIG. 1.

Referring to FIGS. 1 and 2, the electrochemical gas sensor testing device 20 includes an electrochemical cell 10, a test signal generator 18, and a processor 22. The electrochemical cell 10 includes a counter electrode 14, a sensing electrode 12 (which is also known as a working electrode), a reference electrode 13, and a diffusion membrane 6. The electrodes 12, 13, 14 are separated by an ion conductive electrolyte 16. The electrolyte 16 provides ionic electrical conductivity between the electrodes 12 and 14, and electrode 13 such that the electrodes and the electrolyte are in electrical communication with each other. When a gas of interest, i.e., the gas or gases for which the cell system is designed to detect, diffuses through the diffusion membrane 6 and into the electrolyte 16 of the electrochemical cell 10 and contacts the sensing electrode 12, a change in the electric potential of the sensing electrode 12 relative to the counter electrode 14 occurs. The change in electric potential is in response to the change in current flow. The amount of current flowing through the system is proportional to the concentration of the gas of interest sensed by the electrochemical cell 10. The current sensed by the electrochemical cell is converted to a DC signal, which is then transmitted to the processor 22, or other suitable electric signal measuring device, for analysis. After analysis a signal reflecting the concentration of the gas being detected can be sent to a display and expressed, for example, as an absolute value, e.g., in parts per million. The electrochemical gas sensor can be constructed such that when a gas concentration is unacceptably high, an output signal is sent from the sensor indicating that the gas concentration is above a given critical threshold. Other output signals can then be directed to other devices including, e.g., an alarm, which can be in a variety of forms including a light, buzzer or beeper. The electrochemical gas sensor's sensitivity and specificity to a target gas is achieved by varying the composition of the electrodes, electrolyte, the bias voltage, and combinations thereof, of the gas sensor.

The electrochemical cell can be constructed to be capable of detecting any gas of interest according to any suitable methods. Examples of such gases include airborne volatile organic or inorganic compounds including, e.g., oxygen, carbon monoxide, nitrous oxide, ammonia, arsine, tetrahydrofuran, chlorine, diborane, sulfur hexafluoride, silicon tetrachloride, ethanol, methanol, ethyl mercaptan, ethylene, titanium tetrachloride, fluorine, ethylene oxide, hydrogen, hydrogen bromide, hydrogen chloride, hydrogen cyanide, hydrogen fluoride, hydrogen sulfide, methyl mercaptan, nitric oxide, nitrogen dioxide, ozone, sulfur dioxide, hydrogen selenide, hydrogen peroxide, and combinations thereof.

It is noted that the operation of the electrochemical gas sensor has been described for illustrative purposes only. Many variations of electrochemical gas sensor design are known in the art and can be used in conjunction with the electrochemical gas sensor testing device.

Figure 3A:
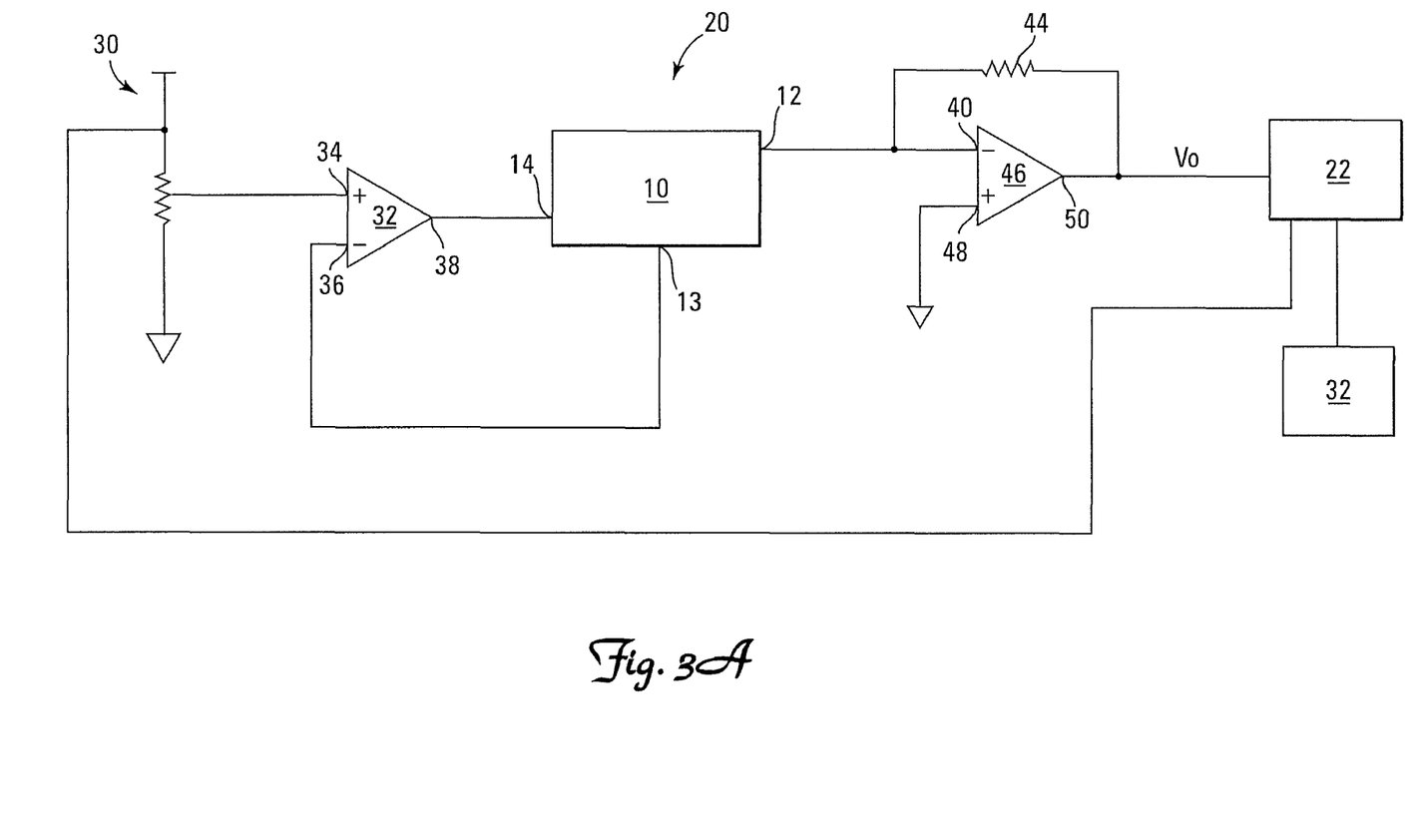
FIG. 3A is a schematic diagram of the electrochemical gas sensor test device of FIG. 1.

Referring to FIG. 3A, the test signal generator 18, which in this embodiment is illustrated as a potentiometer 30, is coupled to the non-inverting input 34 of an operational amplifier 32. A reference electrode 13 is coupled to the inverting input 36 (denoted as −) of the operational amplifier 32. The output 38 of the operational amplifier 32 is coupled to a counter electrode 14 of an electrochemical cell 10. The operational amplifier 32 maintains the reference electrode 13 at the bias potential. The external operating voltage between the sensing electrode 12 and counter electrode 14 is maintained at a sufficient level to drive the electrochemical reaction. The sensing electrode 12 is coupled to the inverting input 40 (denoted as −) of a transimpedance amplifier 46. The non-inverting input 48 (denoted as +) of transimpedance amplifier 46 is connected to ground. The non-inverting input 48 can alternatively can be connected to a reference potential. The sensing electrode 12 is also in electrical communication with the processor 22. A feed back loop that includes a resistor 44 is connected to the sensing electrode 12 and the output 50 of the transimpedance amplifier 46.

In operation, the processor 22 signals the potentiometer 30 to generate a multiplexed signal that includes a direct current bias voltage component and a test signal ($S_{i_a}$) component, which is an alternating current signal that is free of a DC component. The DC bias voltage is applied to the non-inverting input 34 of operational amplifier 32 and maintains the reference electrode 13 of the electrochemical cell 10 at a predetermined voltage. The counter electrode 14 receives the AC test signal generated by the signal generator 30. The AC test signal is transmitted from the counter electrode 14, through the electrolyte 16 of the electrochemical cell 10, to the sensing electrode 12, and then to the processor 22. The signal received by the processor 22 from the sensing electrode includes the AC test signal component ($S_{i_r}$), and, when present, a DC component. The DC component, if present, corresponds to the signal generated by the change in potential resulting from a gas of interest being detected by the electrochemical cell 10, as described above. The processor 22 analyzes each component of the received signal and optionally outputs a signal to a device 32.

Figure 3B:
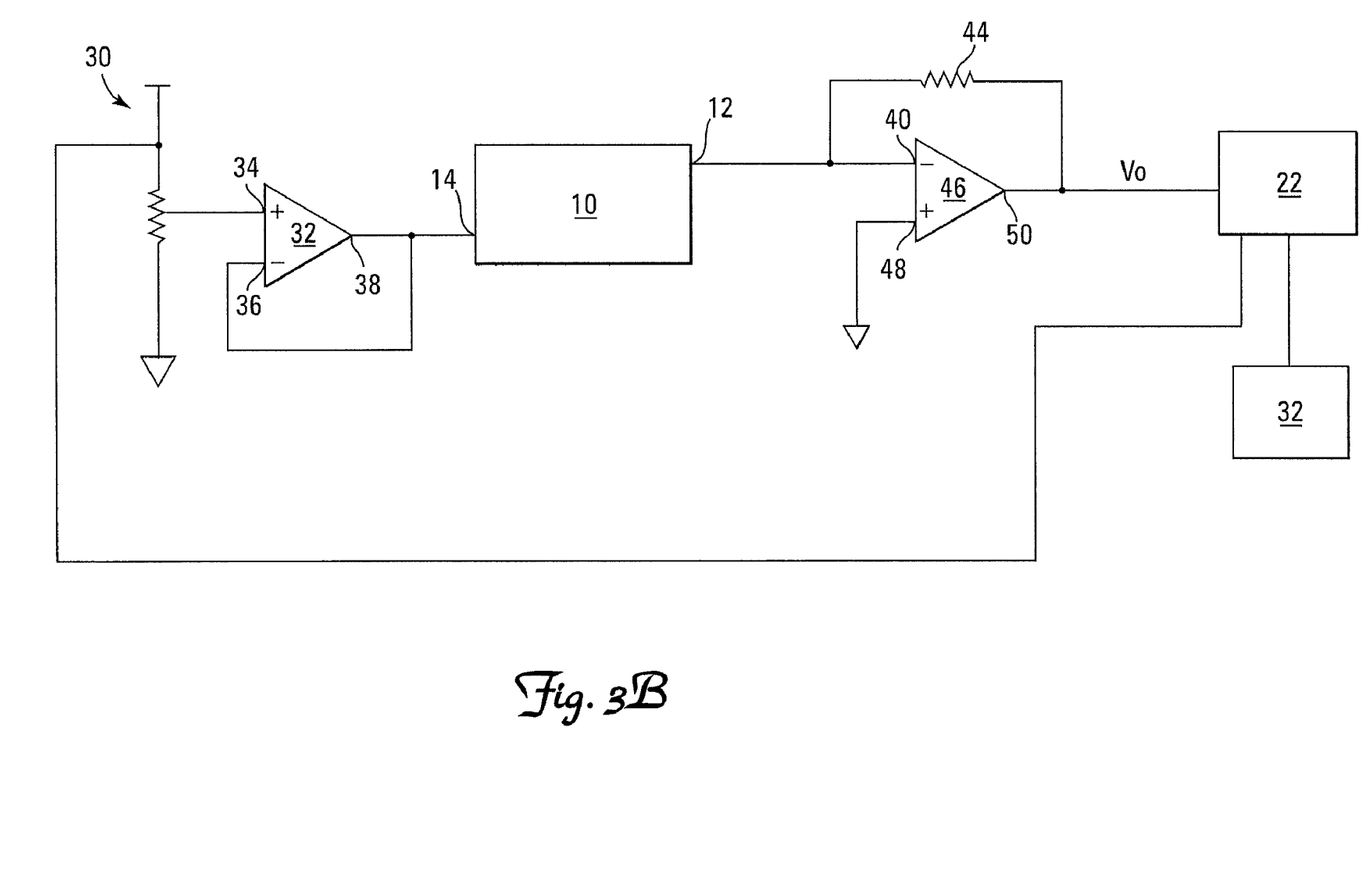
FIG. 3B is a schematic diagram of an electrochemical gas sensor test device that does not include a reference electrode.

FIG. 3B illustrates another embodiment of an electrochemical gas sensor testing device similar in construction and operation to the device of FIG. 3A with the exception that the electrochemical cell 10 does not include a reference electrode and the output 38 of the operational amplifier 32 is transmitted to the negative input 36 of the operational amplifier 32.

Figure 4:
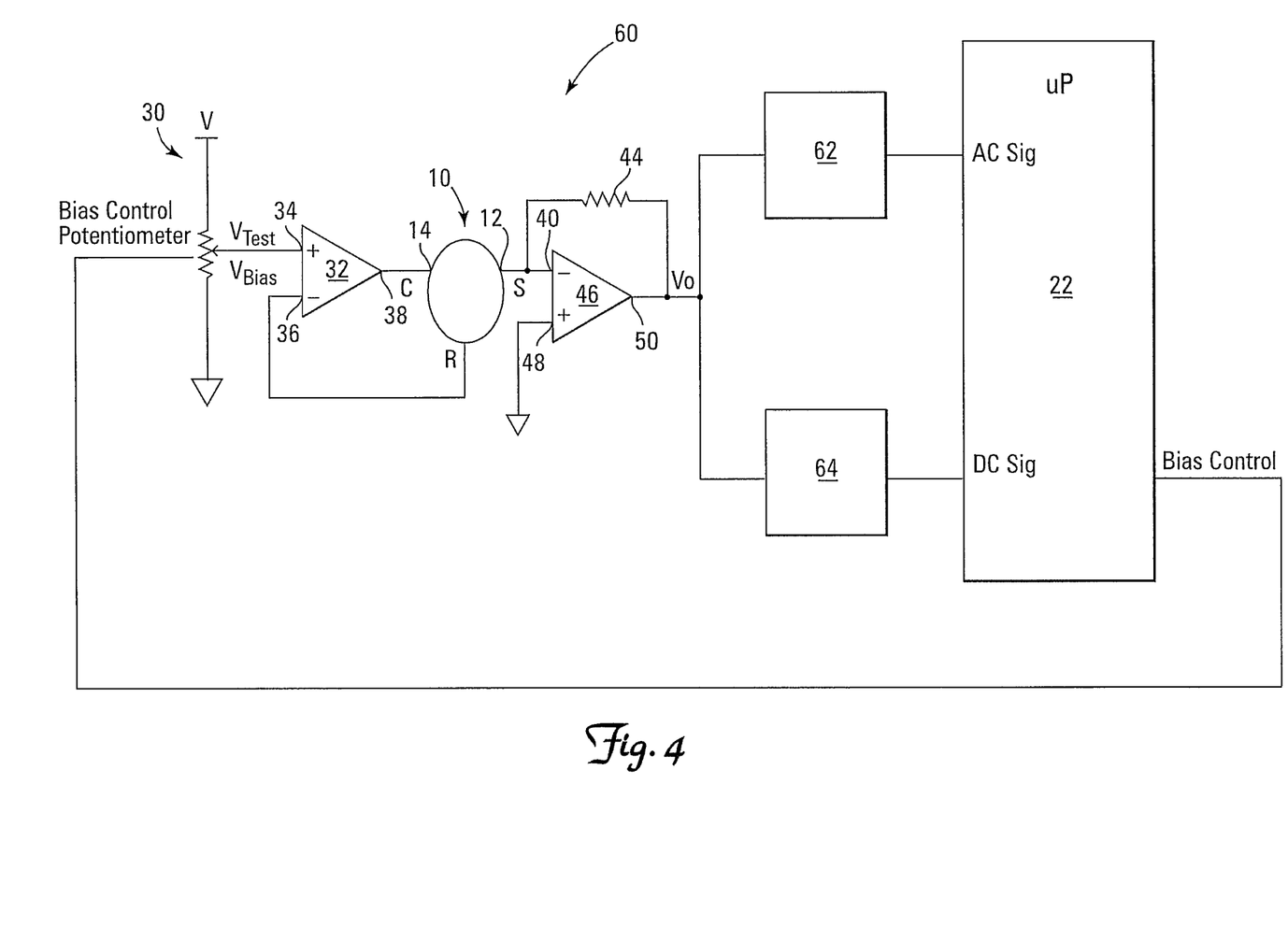
FIG. 4 is a schematic diagram of an electrochemical gas sensor test device according to another embodiment.

FIG. 4 illustrates an embodiment of an electrochemical gas sensor test device 60 that includes a band pass filter 62 and a low pass filter 64. The signal passes from the transimpedance amplifier 46 through the band pass filter 62 and the low pass filter 64 prior to reaching the processor 22. The band pass filter 62 filters out any DC component that is present in the signal and transmits the AC component of the signal to the processor 22 for analysis. The low pass filter 64 prevents the AC component of the signal from passing there through and transmits the DC component of the signal to the processor 22 for analysis.

Figure 5:
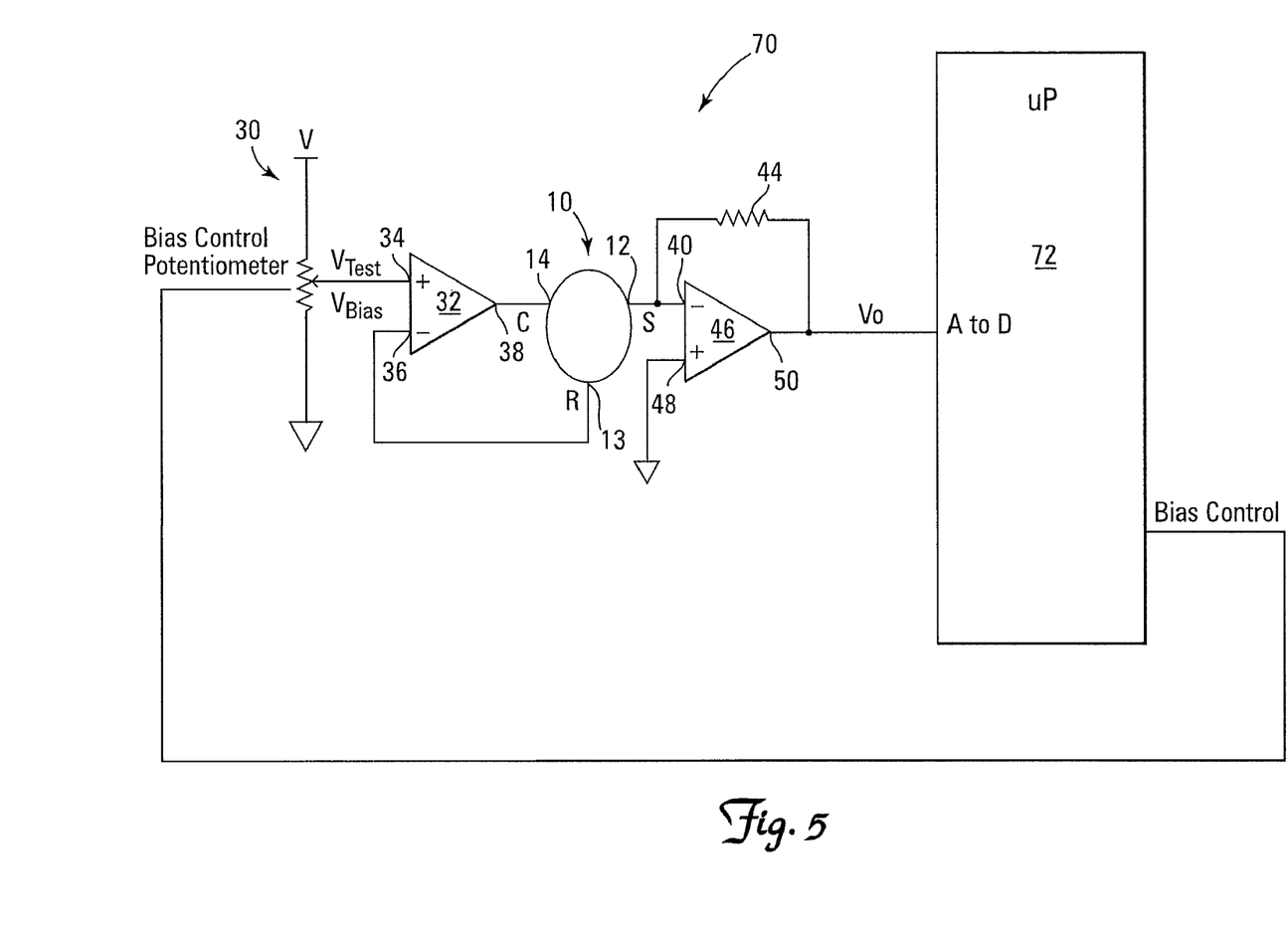
FIG. 5 is a schematic diagram of another embodiment of an electrochemical gas sensor test device.

FIG. 5 illustrates an embodiment of a gas sensor testing device 70 in which the processor 72 is capable of converting the analog signal received from the sensing electrode to a digital signal. The processor 72 then analyzes the AC component of the signal and the DC component of the signal.

In operation, when the AC test signal (S) is received by the processor 22, 72 on cell startup (ti) it can be stored as $S_{ti_r}$. Subsequently (e.g., at time ti+t1) a second AC test signal ($S_{(ti+t1)}$) is generated by the signal generator 30, applied to the non-inverting input 34 of the operational amplifier 32, transmitted across the electrochemical cell 10 to the sensing electrode 14, to the transimpedance amplifier 46, and then received by processor 22, 72 from output 50 of the transimpedance amplifier 46. The test signal ($S_{(ti+t1)r}$) received by the processor 22, 72 from output 50 is then analyzed to determine if any change has occurred in the test signal that is received by the processor 22, 72 at time ti+t1 ($S_{(ti+t1)r}$) relative to the initial test signal ($S_{i_r}$) that is stored in the processor 22, 72. The processor 22, 72 can analyze the signal for a variety of changes relative to the stored signal or a previous signal including, e.g., a change in the frequency of the received signal, a change in the frequency profile of the received signal, a change in the amplitude of the received signal, a change in the amplitude at multiple frequencies of the received signal, and combinations thereof. A change in the signal is indicative of the state of the electrochemical cell, which state can be a relatively diminished cell capacity (i.e., performance), significantly diminished cell capacity, or cell failure. If no signal is received by the processor 22, 72, the cell 10 is deemed to have failed.

Alternatively, the processor 22, 72 instructs the test signal generator 18 to apply a constant test signal (S) to the cell. At a subsequent time (e.g., ti+t1), the processor 22, 72 queries the output 50 of the transimpedance amplifier 46 and receives a second AC test signal ($S_{(ti+t1)r}$). The processor 22, 72 then analyzes the second AC test signal, e.g., by comparing it to the stored initial test signal ($S_{i_r}$).

The processor 22, 72 can perform a number of analyses on the received signal ($S_r$) including, e.g., comparing the amplitude of the received test signal at time i+t1 ($S_{(i+t1)r}$) to that of the amplitude of the received initial test signal ($S_{i_r}$), comparing at least one frequency of the received test signal at time ti+t1 ($S_{(i+t1)r}$) to that of the same at least one frequency of the received initial test signal ($S_{i_r}$), comparing the amplitude-frequency profile of the received test signal at time i+t1 ($S_{(i+t1)r}$) to that of the amplitude-frequency profile of the received initial test signal ($S_{i_r}$), and combinations thereof.

In another embodiment, when the AC test signal that is applied to the cell is received by the processor 22, 72, the processor 22, 72 determines that the cell 10 is functioning and sends a corresponding signal to that effect, and when the applied AC test signal is not received by the processor 22, 72, the processor 22, 72 determines that the cell 10 has failed and sends a corresponding signal to that effect.

Figure 6A:
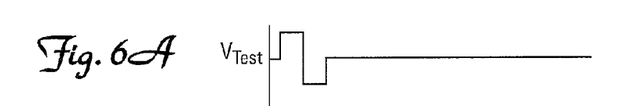
FIG. 6A is a graphical representation of a balanced step test signal (Vtest) applied to an electrochemical cell.
Figures 6B, 6C:
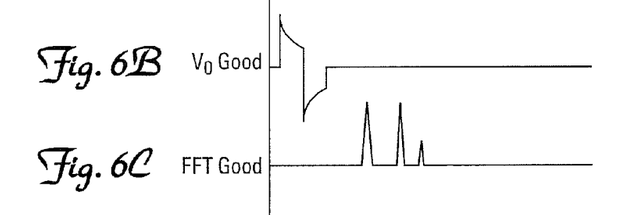
FIG. 6B is a graphical representation of the signal (Vo) at the output of a working electrochemical cell after application of the test signal (Vtest) of FIG. 6A.
FIG. 6C is a graphical representation of the fast Fourier transform of the output signal (Vo) of FIG. 6B.
Figure 6D:
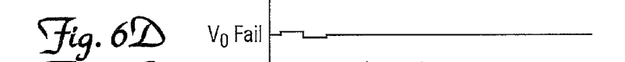
FIG. 6D is a graphical representation of the signal (Vo) at the output of a failed electrochemical cell after application of the test signal (Vtest) of FIG. 6A.
Figure 6E:
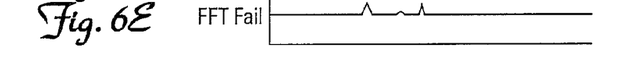
FIG. 6E is a graphical representation of the fast Fourier transform of the output signal (Vo) of FIG. 6D.

In another embodiment, the processor 22, 72 is programmed with code to perform a Fast Fourier Transformation of the signal output from the sensing electrode 12 of the electrochemical cell 10 and received by the processor 22, 72, as illustrated in FIGS. 6A-E. In FIG. 6A, a test signal (Vtest), in the form of a balanced step test signal, is applied to an electrochemical cell. The corresponding output test signal voltage (VoGood) at the transimpedance amplifier of a functioning electrochemical cell, which is graphically represented by FIG. 6B, is then transmitted to processor 22, 72 where a Fast Fourier Transformation (FFT Good) of the output test signal of the working cell is performed, as represented graphically by FIG. 6C. In FIG. 6D, the corresponding output test signal voltage (VoFail) at the transimpedance amplifier of an electrochemical cell that has failed or is failing is transmitted to processor 22, 72, where the Fast Fourier Transformation (FFT Fail) of the output test signal is performed as graphically represented in FIG. 6E. The Fast Fourier Transformation of the received signal is optionally analyzed, stored, and compared to initial and subsequent signals as described herein.

Figure 7A:
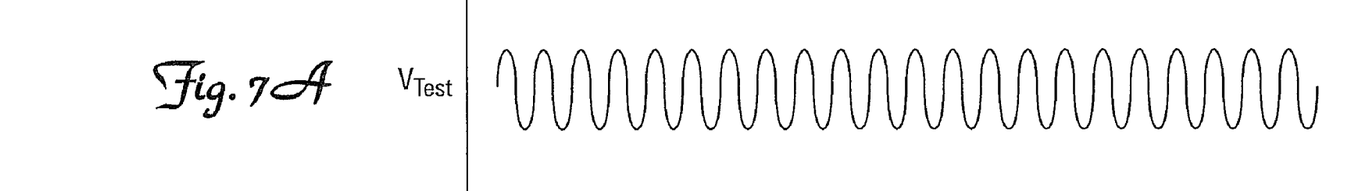
FIGS. 7A-C are, respectively, graphical representations of an input test signal (Vtest) having a constant frequency and amplitude applied to an electrochemical cell, the output signal (VoGood) corresponding to the test signal applied to a working cell, and the output signal (VoFail) corresponding to the test signal applied to a failed cell.
Figure 7B:
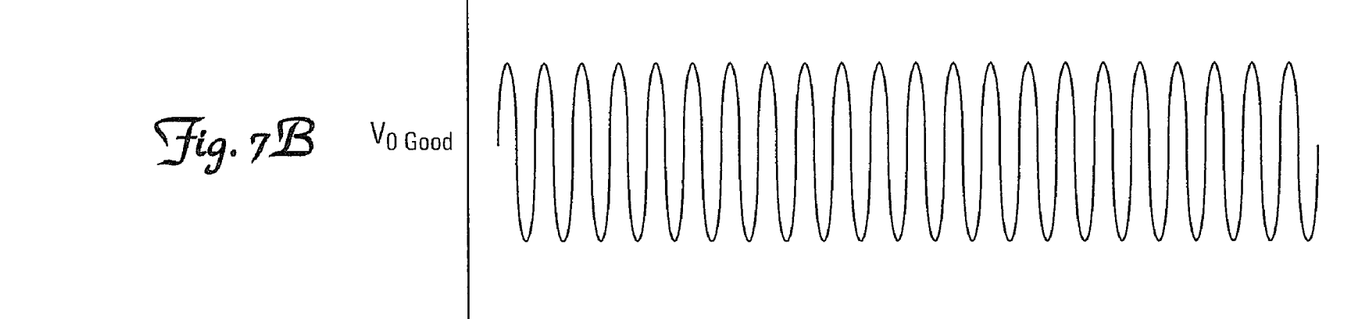
Figure 7C:
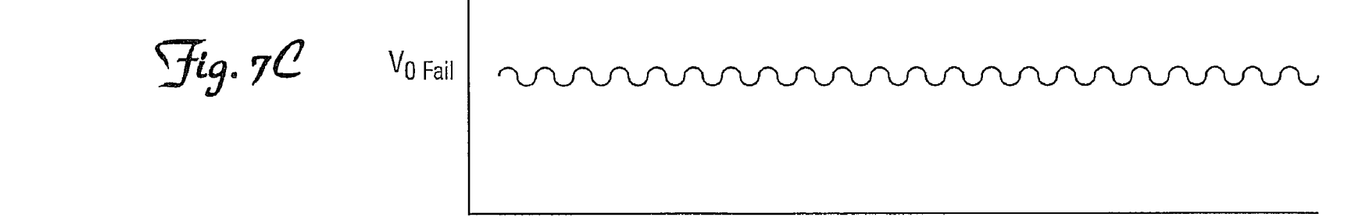

In other embodiments, the applied test signal (VTest) has a constant frequency and amplitude, which is graphically represented by FIG. 7A. During operation, the test signal (VTest) is applied constantly to the electrochemical cell, for an extended period of time or intermittently. The initial test signal applied to the electrochemical cell and received by the processor (VoGood) is stored in a memory. FIG. 7B illustrates the test signal (VoGood) as received by the processor 22, 72 when the cell is functioning. At a subsequent time the processor 22, 72 compares the received test signal to the stored test signal. The comparison can include a comparison of the amplitude of the test signal to the corresponding amplitude of the initial stored test signal. The processor can additionally store a test signal received at a time subsequent to the initial time in memory for any suitable purpose including comparison to a previous or subsequent test signal. When the processor determines that the amplitude of the received signal is reduced relative to the amplitude of the initial signal, a signal indicating that a failed cell condition exists is generated and can be sent to any suitable destination directly or remotely including, e.g., a display, a printer, an individual, or other device. FIG. 7C illustrates a test signal (VoFail) as received by the processor when the cell has failed. The AC test signal does not interfere with the DC signal that occurs as a result of gas detection by the electrochemical cell of the sensor.

Figure 8A:
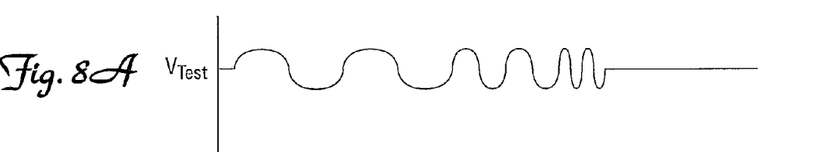
FIGS. 8A-8B are, respectively, graphical representations of a multi-frequency test signal (Vtest) applied to an electrochemical cell and the corresponding output signal (Vo) received from the electrochemical cell.
Figure 8B:
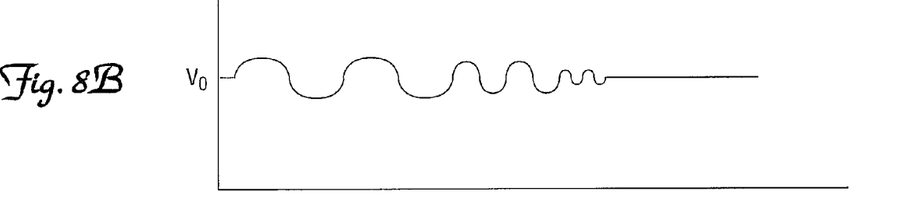

FIGS. 8A and 8B illustrate a test signal (Vtest) in the form of a frequency burst that includes multiple frequencies. The frequency burst signal (Vtest) is applied to the electrochemical cell, received by the processor, and stored in a memory. At a subsequent time the processor analyzes a newly received test signal (Vo) and compares the received test signal to the stored test signal. The comparison can include a comparison of the amplitude of the test signal at any point along the signal profile, to the corresponding amplitude of the initial stored test signal. Optionally a test signal received at a time subsequent to the initial time is stored in memory for any suitable purpose including comparison to previous or subsequent test signals. When the processor determines that the amplitude or frequency of the signal is reduced relative to the amplitude or corresponding frequency of the initial signal, an appropriate signal (e.g., a failed or failing cell condition exists) can be sent to any suitable destination directly or remotely including, e.g., a display, an individual, or other device. A failed cell will typically show reduced amplitudes at all frequencies, particularly at lower frequencies. The AC test signal does not interfere with the DC signal that occurs as a result of gas detection by the electrochemical cell of the sensor.

The processor 22, 72 optionally sends a signal to a display 64 (e.g., an LED display and/or an LCD display), a remote device, an individual (including, e.g., directly, remotely or both) or a combination thereof. Depending on the nature of the change in the detected signal, the signal sent by the processor 22, 72 can be in the form of a status update, a warning, an alarm indicating that the sensor needs to be checked, e.g., is failing or has failed. In addition the standard signals provided by the sensor related to gas detection, e.g., an alarm, the concentration of the gas detected, typically in parts per million (ppm), or any appropriate message can be sent to the display, a remote location, an individual or a combination thereof.

It will be apparent to those skilled in the art that many design variations are possible for the method of testing electrochemical gas sensors and the electrochemical gas sensor test circuits disclosed herein. All patents disclosed herein are hereby incorporated herein.

Other embodiments are within the claims. The electrochemical gas sensor testing device, for example can be in the form of a module that is interchangeable with other components to form a unit. Although the signal generator has been described as a potentiometer, the signal generator could alternatively or in addition be a variable gain amplifier. In some embodiments, for example, the sensor can include additional electrodes, e.g., electrodes that provide means to detect more than one gas or to reduce or null out the effects of interfering gases. Although the electrochemical cell and test device have been described as including a potentiometer to control of the potential of the counter electrode, the device can alternatively be configured such that the potentiometer controls the potential of the working electrode.

The processes and the signals and data that are described above as being provided by or performed by the processor can be transmitted and performed to and by a variety of devices including, e.g., networks, base stations, mobile phones, laptop computers, handheld computing devices, and personal digital assistants (PDA's). The processor can include a microprocessor, a digital signal processor, field programmable gate array, application specific integrated circuit or similar hardware, discrete logic circuitry, firmware and/or software for implementing the techniques described herein. Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and combinations thereof. In some embodiments, memory stores program instructions that, when executed by the processor, cause the module, the electrochemical cell, the circuitry of the electrochemical cell, the processor or a combination thereof to perform the functions attributed to them herein. If implemented in software, a computer-readable medium may store computer readable instructions, i.e., program code, that can be executed by a processor or digital signal processor to carry out one of more of the techniques described above. For example, the computer-readable medium may include random access memory, read-only memory, non-volatile random access memory, and electrically erasable programmable read-only memory, flash memory and combinations thereof. The computer-readable medium may include computer readable instructions that when executed in a wireless communication device, cause the wireless communication device to carry out one or more of the techniques described herein.

What is claimed is:

1. A method of testing an electrochemical gas sensor, said method comprising:
simultaneously applying
an alternating current (AC) test signal having a frequency and amplitude and
a direct current (DC) bias voltage to a counter electrode of an electrochemical gas sensor, the electrochemical gas sensor comprising
a sensing electrode,
an electrolyte, and
the counter electrode;

transmitting an AC test signal from the sensing electrode to a processor;
comparing the AC test signal received by the processor to a stored AC test signal having a frequency and amplitude; and
determining whether or not the electrochemical cell is functioning,
the applied AC test signal remaining constant over time and the stored AC test signal remaining constant over time,
wherein the electrochemical cell is determined to not be functioning properly when the amplitude or frequency of the AC test signal received by the processor is reduced relative to the stored AC test signal.

2. The method of claim 1 further comprising comparing at least one frequency of a first AC signal corresponding to the AC test signal transmitted to the processor at a first time to the same at least one frequency of a second AC signal corresponding to the AC test signal transmitted to the processor at a second time later than the first time.

3. The method of claim 1 further comprising simultaneously analyzing a DC signal corresponding to the concentration of a gas present in the electrochemical cell and the AC signal corresponding to the AC test signal.

4. The method of claim 1, wherein said processor simultaneously receives a DC signal corresponding to the concentration of a gas present in the electrochemical cell and an AC signal corresponding to the AC test signal.

5. The method of claim 1 further comprising storing an AC signal corresponding to the AC test signal.

6. The method of claim 5 further comprising comparing a frequency of a received AC signal corresponding to the AC test signal to the stored AC signal.

7. The method of claim 1, wherein when no AC signal corresponding to the AC test signal is received by the processor, a signal is generated indicating that the cell is not functioning properly.

8. The method of claim 1, wherein said AC signal corresponding to said AC test signal comprises multiple frequencies.

9. The method of claim 1, wherein said AC signal corresponding to said AC test signal comprises constant frequency and amplitude.

10. The method of claim 1 further comprising applying the AC test signal continuously to said electrochemical cell.

11. The method of claim 1, wherein the comparing comprises comparing the amplitude of the AC signal corresponding to the AC test signal received by the processor with the amplitude of the stored AC test signal.

12. The method of claim 1 further comprising periodically applying the AC test signal and comparing the amplitude of the applied AC test signal to the stored AC test signal.

13. The method of claim 1 further comprising continuously applying the AC test signal and comparing the amplitude of the applied AC test signal to the amplitude of the stored AC test signal.

14. A method of testing an electrochemical sensor, said method comprising:
simultaneously applying an alternating current (AC) test signal and a direct current (DC) bias voltage to a counter electrode of an electrochemical gas sensor, the electrochemical gas sensor comprising
a sensing electrode,
an electrolyte, and
the counter electrode, and
a membrane;
transmitting an AC test signal from the sensing electrode to a processor;
comparing the AC test signal received by the processor with a stored AC test signal; and
determining whether or not the electrochemical cell is functioning,
wherein the electrochemical cell is determined to not be functioning properly when the amplitude or frequency of the AC test signal received by the processor is reduced relative to the stored AC test signal.

* * * * *

UNITED STATES PATENT AND TRADEMARK OFFICE
CERTIFICATE OF CORRECTION

PATENT NO. : 8,097,146 B2
APPLICATION NO. : 12/056876
DATED : January 17, 2012
INVENTOR(S) : Patrick G. Smith It is certified that error appears in the above-identified patent and that said Letters Patent is hereby corrected as shown below:

Col. 10, line 27:
In claim 14, line 11, the phrase "transmitting an AC test signal" should read --transmitting the AC test signal--.

Signed and Sealed this
Thirteenth Day of March, 2012

David J. Kappos
*Director of the United States Patent and Trademark Office*